United States Patent [19]

Huffman et al.

[11] Patent Number: 5,434,152
[45] Date of Patent: Jul. 18, 1995

[54] ASYMMETRIC SYNTHESIS OF (S)-(−)-6-CHLORO-4-CYCLOPROPYL-3,4-DIHYDRO-4-[(2-PYRIDYL)ETHYNYL]-2(1H)-QUINAZOLINONE

[75] Inventors: Mark A. Huffman, Scotch Plains; Nobuyoshi Yasuda, Mountainside; Ann E. DeCamp, Scotch Plains; Edward J. J. Grabowski, Westfield, all of N.J.

[73] Assignee: Merck & Co., Inc., Rahway, N.J.

[21] Appl. No.: 148,476

[22] Filed: Nov. 8, 1993

[51] Int. Cl.⁶ .............. A61K 31/535; A61K 31/505; C07D 265/24; C07D 265/14
[52] U.S. Cl. .............................. 514/234.5; 514/253; 514/259; 544/110; 544/238; 544/254; 544/286
[58] Field of Search .............. 544/110, 238, 254, 286; 514/253, 259, 234.5

[56] References Cited

PUBLICATIONS

Mukaiyama T., et al., "Enantioselective Addition of Acetylene To Aldehyde", Chemistry Letters, pp. 447–448, 1979.
Niwa, S., et al., "Catalytic Asymmetric Synthesis of Optically . . . ", J. Chem. Soc. Perkin Trans. 1 1990, pp. 937–943.
Corey, E. J. "Studies On Enantioselective Synthesis", Abstracts, 33rd National Organic Chemistry, Symposium, Jun. 13–17, 1993.
Kijima, M. et al., "Table I. Reaction of photoactivated Alkylcobaloxime and Ethyl Mercaptoacetate", J. Org. Chem. 1988, 53, 4148–4149.
Tomioka, K., et al., "Catalytic Asymmetric Addition of Organolithiums to Aldimines", Tetrahedron Letters, vol. 32, No. 26, pp. 3095–3098, 1991.
Tomioka, K., et al., "Asymmetric Synthesis Utilizing External Chiral Ligands", Review, pp. 541–549, Jul. 1990.
Wynberg, H., "Asymmetric Catalysis by Alkaloids", Stereochemistry, vol. 16, pp. 87–128.
Blaser, Hans–Ulrich, "The Chiral Pool as a Source of Enantioselective Catalysts and Auxiliaries," Chem. Rev. 1992, 92, 935–952.
Leyendecker, F., et al., "Faceurs Controlant LaReconnaissance Enantioselective . . . ", Nouv. J. Chim., 9, 13, 1985.
Imamoto, T., et al., "Enantioface-Differentiating 1,4-Addition . . . ", Chemistry Letters, pp. 45–46, 1980.

Primary Examiner—Mukund J. Shah
Assistant Examiner—Matthew V. Grumbling
Attorney, Agent, or Firm—Roy D. Meredith; Jack L. Tribble

[57] ABSTRACT

An asymmetric synthesis of (S)-(-)-6-chloro-4-cyclopropyl-3,4-dihydro-4-[(2-pyridyl)ethynyl]-2(1H)-quinazolinone comprises the chiral addition of 2-pyridylacetylide to N¹-protected 6-chloro-4-cyclopropyl-2-quinazolinone followed by removal of the protecting group.

12 Claims, No Drawings

ASYMMETRIC SYNTHESIS OF (S)-(−)-6-CHLORO-4-CYCLOPROPYL-3,4-DIHYDRO-4-[(2-PYRIDYL)ETHYNYL]-2(1H)-QUINAZOLINONE

BACKGROUND OF THE INVENTION

This case is related to U.S. Ser. No. 07/991,164, filed Dec. 16, 1992; Merck cases 19043 and 19060.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of AIDS and similar diseases, e.g., azidothymidine or AZT.

This invention relates to an improved process for synthesizing the AIDS antiviral L-738,372, which is a chiral compound of the following chemical structure, 10:

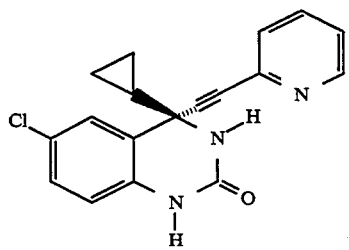

The substituted quinazoline L-738,372 is an exceptionally potent inhibitor of HIV reverse transcriptase. This activity of the compound makes it useful in the treatment or prevention of AIDS. The present invention describes an improved synthesis of this compound.

The present invention describes the novel reaction of an acetylide with a cyclic N-acylated ketimine. There is a general lack of literature precedent on the asymmetric addition of acetylide nucleophiles, especially to imine derivatives as in the present invention.

The only related chiral acetylide additions have been to aldehydes. Mukaiyama (Chemistry Letters, 447(1979)) reported the addition of acetylides to aldehyde substrates in the presence of a diamine chiral modifier. The asymmetric addition of dialkynylzinc reagents to aldehydes in modest enantiomeric excess has been disclosed by Soai (Journal of the Chemical Society, Perkin Transactions 1,937(1990)). Recently, Corey reported the asymmetric addition of acetylides to aldehydes, catalyzed by chiral oxazaborolidines (Abstracts, 33rd National Organic Chemistry Symposium, June 13-17, 1993, Bozeman, Montana, FIG. 21). In the present invention, the substrate is unique in that an acetylide is added to a cyclic N-acylated ketimine rather than a simple aldehyde.

Tomioka [Tetrahedron Letters, 32, 3095(1991); Tetrahedron Letters 31,6681 (1990); Synthesis, 541 (1990)] reports the chiral addition of alkyl and vinyl lithiums (but not acetylides) to relatively unhindered, acylic aldimines in the presence of chiral amino ethers. Amino ethers do not function effectively in the present process.

The use of alkaloids (including the cinchona alkaloids quinine and dihydroquinine) in asymmetric synthesis was reviewed by H. Wyberg, "Asymmetric Catalysis by Alkaloids," in E.L. Eliel (Ed.), Topics in Stereochemistry, Vol. 16, Wiley and Sons, pp. 87–129 and by Blaser (Chemistry Reviews, 92, 935(1992)). No precedent for the chiral addition of acetylides to cyclic ketimines is reported.

SUMMARY OF THE INVENTION

This invention is concerned with a novel process for the asymmetric synthesis of compound 10 via chiral addition of lithium 2-pyridyl acetylide to the $N^1$-protected quinazolinone of structure 7,

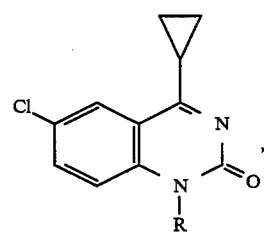

wherein R is a protecting group. The reaction is carried out under the chiral modifying influence of the lithium alkoxide of quinine or dihydroquinine followed by removal of the protective group.

DETAILED DESCRIPTION OF THE INVENTION

The novel process of this invention is represented by the following reaction scheme:

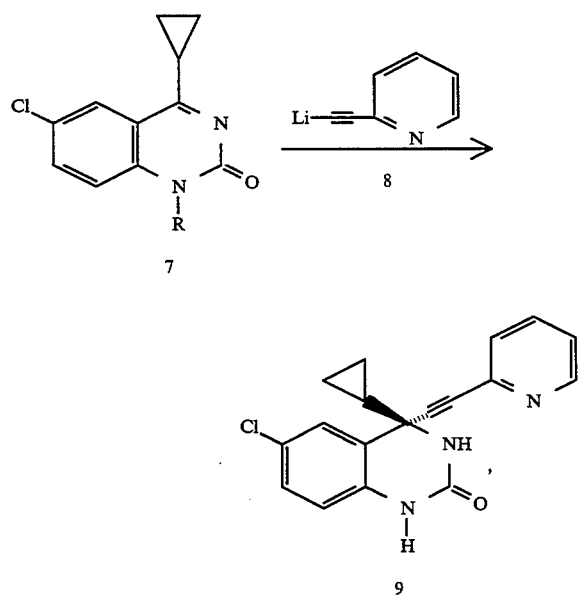

wherein R is a protecting group and R is defined as —CH₂—A, and A is i) phenyl unsubstituted or substituted one or more times with B, wherein B is $C_{1-4}$ alkyl, $C_{1-4}$ alkoxy, or halo;

ii) naphthyl unsubstituted or substituted one or more times with B; or iii) anthryl unsubstituted or substituted one or more times with B.

The present invention relates to a process for the preparation of a compound of structural formula:

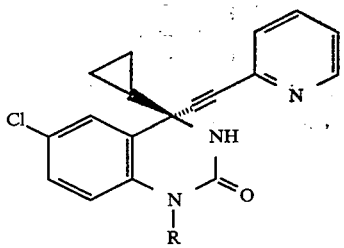

I wherein R is —CH$_2$—A, and A is i) phenyl unsubstituted or substituted one or more times with B, wherein B is C$_{1-4}$ alkyl, C$_{1-4}$ alkoxy, or halo;

ii) naphthyl unsubstituted or substituted one or more times with B; or iii) anthryl unsubstituted or substituted one or more times with B;

said process comprising the steps of:

(a) mixing one equivalent of 2-ethynylpyridine with about one equivalent of a chiral modifier selected from quinine or dihydroquinine, in a solvent comprising an ethereal solvent selected from THF, diethyl ether, 1,2-dimethoxyethane, or dioxane, said ethereal solvent optionally combined with toluene, hexanes, or other less polar solvents;

(b) mixing thereto, at between about −70° to about −20° C., two or more equivalents of either n-butyl lithium or lithium hexamethyldisilazane;

(c) mixing thereto, 0.5 to 1.0 equivalent of a compound of structural formula

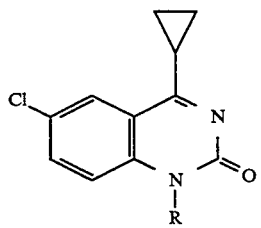

7 at about −50° to 0° C.;

(c) maintaining the resulting mixture at about −40° C. to about 0° C. for 2-24 hours;

(d) to give a compound of Formula I.

An important intermediate in the process of the present invention is the lithium alkoxide salt of the chiral modifier. The intermediate is illustrated by formula A of the following structure:

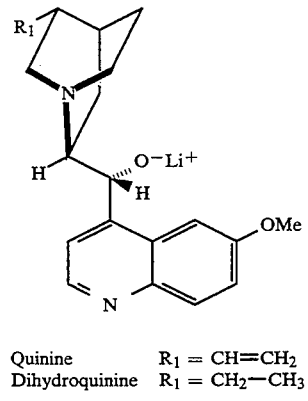

A

Quinine R$_1$ = CH=CH$_2$
Dihydroquinine R$_1$ = CH$_2$—CH$_3$

In one embodiment the process comprises treating a mixture of a chiral modifier such as quinine or dihydroquinine, and 2-ethynylpyridine 8, in an ethereal solvent such as THF, diethyl ether or 1,2-dimethoxyethane in combination with toluene or hexanes, or other non-polar solvents at about −70° C. to about −20° C. with n-butyl lithium or lithium hexamethyl-disilazane, followed by treatment with 7 at about −50° to 0° C., followed by warming to about −40° C. to 0° C. and maintaining at that temperature for about 2-24 hours. The reaction is carded out at an alkyne concentration in the range of 5 to 300 mM.

The less polar solvents used in the reaction of the present invention include, but are not limited to, diethyl ether, benzene, n-hexane, n-octane, toluene, and cyclohexane. "Halo" includes bromo, chloro and iodo.

Applicants have found that addition of the lithium acetylide to 7 in the presence of lithium alkoxides of cinchona alkaloids proceeds with asymmetric induction. The desired enantiomer forms in excess when quinine, dihydroquinine, or cinchonidine is used. The pseudoenantiomeric compounds quinidine and dihydroquinidine favor the other enantiomer. The use of magnesium or sodium in place of lithium gives much lower selectivity and reverses the sense of selectivity. All other types of ligands tested gave very little, if any, enantioselectivity. Overall assay chemical yields are generally unaffected by the presence of ligands, and are uniformly high. For the paramethoxybenzyl protecting (PMB) group, results are summarized as in the Table of Example 1.

In the most preferred process of this invention, the compound of structural formula:

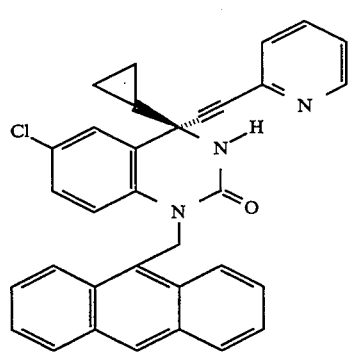

II

;

is prepared by the process comprising the steps of:

(a) mixing in a solvent comprising THF, about one equivalent of 2-ethynylpyridine with about one equivalent of the chiral modifier quinine;

(b) cooling the mixture to between about −40° C. and about −60° C.;

(c) adding thereto about 2.0 equivalents of n-butyllithium;

(d) warming the reaction mixture to about −25° C.;

(e) adding between about 0.5 to 1.0 equivalents of the quinazolinone

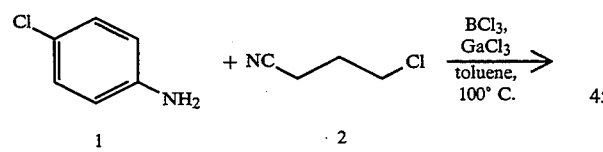

(f) stirring the resulting mixture at about −25° C. for about 16 hours to give the compound of formula II.

Preparation of the starting material 7 and removal of the protecting group are fully described in Examples that follow and proceed in accordance with the following reaction scheme.

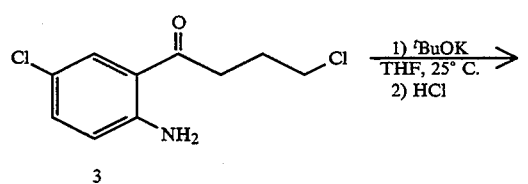

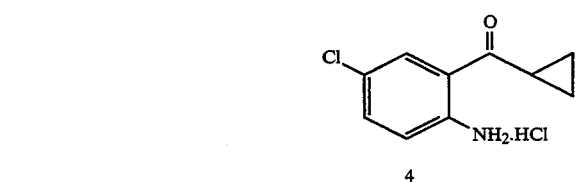

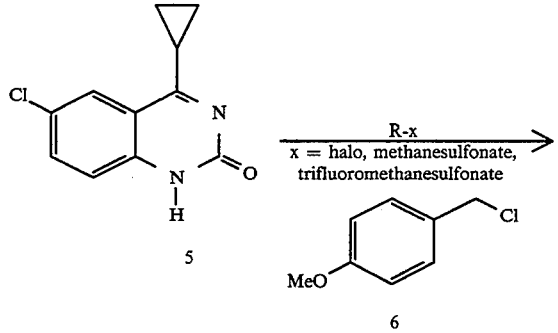

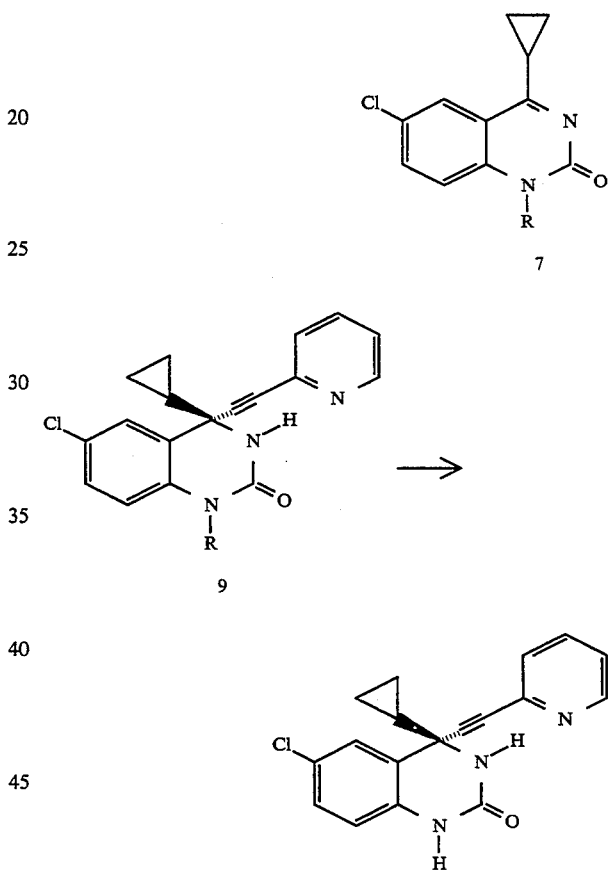

Compound 10 is useful in the inhibition of HIV reverse transcriptase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The particular advantage of Compound 10 is its potent inhibition against HIV reverse transcriptase rendered resistant to other antivirals, such as 3-([(4,7- dichloro- 1,3-benzoxazol-2-yl)methyl]amino)-5-ethyl-6-methyl-pyridin-2(1H)-one; or 3-[2-(1,3-benzoxazol-2-yl)ethyl]-5-ethyl-6-methyl-pyridin-2(1H)-one; or AZT.

Compound 10 is also useful in the preparation and execution of screening assays for antiviral compounds. For example, it is useful for isolating enzyme mutants, which are excellent screening tools for more powerful antiviral compounds. Furthermore, it is useful in establishing or determining the binding site of other antivirals to HIV reverse transcriptase, e.g., by competitive inhibition.

For these purposes, Compound 10 may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carders, adjuvants and vehicles.

Compound 10 can be administered orally to humans in a dosage range of 0.1 to 100 mg/kg body weight in divided doses. One preferred dosage range is 0.1 to 10 mg/kg body weight orally in divided doses. Another preferred dosage range is 0.1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

STARTING MATERIAL

Preparation of Ketone 3

To a dry 50 L three neck round bottom flask was charged 10.6 L of dry toluene (KF<100 μg/mL) under ice-MeOH cooling. To this solution was added boron trichloride gas (1.42 kg), keeping the temperature under 7° C.

To a 22 L three neck round bottom flask, equipped with a nitrogen inlet and an overhead stirrer, was added dry toluene (10.2 L, KF<100 μg/mL). To this solution was added 2.214 kg of 4-chloroaniline. The mixture was warmed up to 55° C. to give a homogeneous solution. The solution was cooled to 10°–20° C.

The solution of 4-chloroaniline was transferred into the 10 L dropping funnel and added to the solution of boron trichloride, keeping the temperature below 10° C. with a dry ice-acetone bath.

The suspension was stirred at room temperature for 30 minutes. To this suspension was added 4-chlorobutyronitrile (991 mL, 11 mole), in one portion, under a nitrogen atmosphere.

After 30 minutes of stirring, gallium trichloride (2.324 kg) was added to the mixture under nitrogen atmosphere. The resulting exothermic reaction raised the temperature of the mixture to about 40° C. This solution was stirred at 100° C. for 5 hours, giving a biphasic reaction mixture (70–75% yield). The solution was cooled to 40° C. The solution was diluted with toluene (3 L) and DI water (11 L). The organic phase was separated. The pH of the aqueous layer was 0.2. The organic layer was washed with DI water (11 L) to remove 4-chloroaniline. The final organic layer (25 L) contained 70 mg/mL of the product (1800 g; 72% yield). The solution was concentrated under reduced pressure to give 16 L of a 113 mg/mL (0.5 M) solution of the product (KF<170 μg/mL).

Preparation of 4

To a 50 L cylinder flask, equipped with a thermocouple, a nitrogen inlet, and an overhead stirrer, was added a solution of 4-chloro-2-(4chloro-1-oxobutyl) aniline in a mixture of toluene and THF (4.99 L, containing the starting material 1.2 kg in toluene 3.75 L and THF 1.25 L), dry THF (8.95 L), dry toluene (6.45 L). This solution was cooled to 0°–5° C. To the solution was added potassium t-butoxide (672 g; 5.99 mol) under nitrogen atmosphere. The mixture was warmed to room temperature (20°–25° C.) and stirred for 1 hour. The starting material assayed to be below 0.5 A % by HPLC. Water (16 L) and sodium chloride (2.6 kg) were added and the mixture stirred at 25° C. for 20 minutes. The organic layer was separated and dried via distillation, to give a solution (7.3 L, 81 v/v % toluene/19 v/v % THF) of the desired cyclopropyl ketone (976 g; 96.7% yield). The free aniline was converted to the corresponding hydrochloride salt as follows. To a 50 L cylinder flask, equipped with a thermocouple probe, a nitrogen inlet, and an overhead stirrer, was added the solution of 4-chloro-2-cyclopropylcarbonyl-aniline in toluene/THF. Additional dry toluene (13.2 L) and dry THF (15.6 L) were added. To this solution at 25° C. was added hydrochloric acid (2.55 M HCl in THF; 2.31 L), and the mixture was aged at 25° C. for 1 hour. The mixture was then cooled to 0°–5° C., and aged for 1 hour. The batch was filtered and washed with 2×8.5 L hexane. The solids were dried in a vacuum oven at 30°–35° C., giving 1.071 kg (93%) of hydrochloride salt.

Preparation of 5

Acetic acid (23.1 L) was added to a 100 L cylinder flask, equipped with a thermocouple probe, a nitrogen inlet, and an overhead stirrer, and cooled to 15° C. 4-Chloro-2-cyclopropylcarbonylaniline hydrochloride was added portionwise. To the resulting slurry at 15°–20° C. was added a solution of KOCN (2.52 M; 964.7 g in 4.73 L of water). A homogeneous solution resulted. The mixture was stirred at 25° C. for 1 h. Water (46.0 L) was added, the mixture was aged at 25° C. for 1 h, then cooled to 0°–5° C. The solids were filtered, washed with 2×20 L water (5°–10° C.), and dried in a vacuum oven at 30°–35° C., to give 926 g (93% yield).

Preparation of 7 (R=4-methoxybenzyl)

NaI (10.2 g, 68.03 mmol) was dried by heating to +80° C. under high vacuum for 4 hours.

The quinazolinone, 5, (10 g, 45.35 mmol) was azeotropically dried with toluene and then dissolved in DMF (80 ml). The reaction vessel was cooled to 0° C. and LHMDS (55 ml, 55.0 mmol) was added, maintaining the temperature below +5° C. After 15–30 minutes, 4-methoxybenzyl chloride, 6, (8 ml, 59.0 mmol) was added, followed by NaI (10.2 g, 68.03 mmol). The cooling bath was then removed and the reaction was allowed to warm to RT. The reaction was heated to 60° C. and allowed to age overnight at 60° C. With approximately 2% A of starting material (5) present, the reaction mixture was cooled to RT, concentrated in vacuo, and the concentrate was flushed with acetonitrile (2×50 ml). Acetonitrile (140 ml) was then added to the concentrate, with stirring, followed by slow addition of water (70 ml). The resulting slurry was allowed to stir for 10 minutes and the product was filtered. The cake was washed with acetonitrile-water (75 ml, 2:1) and dried in vacuo (40° C.) giving 7, 11.3 g (73%).

Preparation of 7 (R=9-anthrylmethyl)

Into a dry 75 liter round bottom flask equipped with a 5 L addition funnel, a thermocouple probe, and a nitrogen inlet, were charged 8 L of dry THF. The air in the reaction flask was completely exchanged by three vacuum purges with nitrogen. With stirring, 870 gram of 6-chloro-4-cyclopropylquinazolin-2(1H)-one (96 wt %; 3.79 mol) was added. To the suspension was added 2.30 L of dry N,N-dimethylformamide and an additional 8 L of dry THF. To the suspension was slowly added a solution of lithium bis(trimethylsilyl)-amide in tetrahydrofuran (1 M; 4.28 L), keeping the batch temperature below 27° C. After 900 mL of the solution was added, the reaction mixture became homogeneous. At this point, the addition was stopped and the reaction mixture was stirred at 25° C. for 5 minutes. The addition was resumed keeping the temperature below 27° C. During the addition, the reaction mixture became heterogeneous again. After the mixture was stirred for 30 minutes at room temperature (ca. 23° C.), sodium iodide (743 g; 4.96 mole) and 9-chloromethylanthracene (965 g; 4.26 mole) were added (0.9 L of dry tetrahydrofuran was used for rinse). The mixture was stirred at room temperature for 24 hours. To the reaction mixture was added 20 L of precooled water (at 5° C.) and 7 L of ambient temperature water, keeping the batch temperature below 22° C. The resulting mixture was stirred at room temperature for 3 hours. The precipitates were collected by filtration, washed successively with 10 L of water and 2×5 L of methanol. The crude material was slurried with methanol (13 L) at room temperature for 4 hours, filtered off, washed with 3 L of methanol, and dried in a vacuum oven at 35° C. with a nitrogen sweep to give 1.44 kg of crude product. The crude product was slurried with butyl chloride (13 L) at room temperature for 5.5 hours, filtered off, washed with 4 L of butyl chloride and dried in an oven at 37° C. under house vacuum with nitrogen sweep overnight to give 1.24 kg of the product. The product was stirred in 13 L of methanol at room temperature for 6 hours and the crystals were filtered off, washed with 4 L of methanol, and dried in an oven at 37° C. under house vacuum and nitrogen sweep overnight to give 1.21 kg (85 % yield) of the product.

EXAMPLE 1

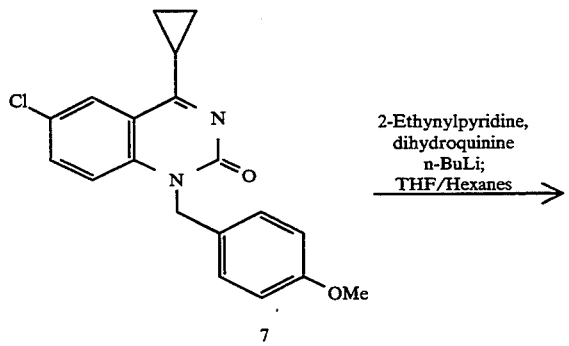

7

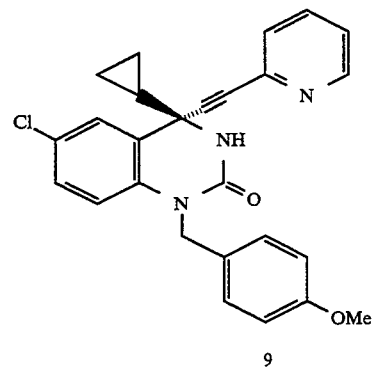

9

2-Ethynylpyridine (76 μL, 77 mg, 0.75 mmol) and dihydroquinine (261 mg, 0.80 mmol) were dissolved in dry tetrahydrofuran (5 mL) under an atmosphere of dry nitrogen. The solution was cooled to −65° C. and treated dropwise with n-butyllithium (1.0 mL of 1.6 M solution in hexanes, 1.6 mmol). The solution was then warmed to −45° C. over a period of 60 min. Hexanes (4 mL) was added followed by 1 mL additional tetrahydrofuran. The solid quinazolinone 7 (170 mg, 0.50 mmol) was then added, and the resulting suspension was warmed to −15° C. After stirring for 3.5 hours at −15° C., the reaction mixture was quenched with 1 N HCl. The mixture was partitioned between CH$_2$Cl$_2$ and 1 N HCl. The aqueous layer was extracted again with CH$_2$Cl$_2$. The combined organic layers were dried over MgSO$_4$ and the solvent was evaporated under reduced pressure, giving a white foam (212 mg). HPLC analysis (Sumichiral OA4700 column 4×250 mm; mobile phase 96:4:0.2 hexanes/ethanol/trifluoro-acetic acid; flow rate 1.0 ml/min) showed 9% residual 7 (18.8 min), 82.4% 9 (21.4 min) and 7.8% of the other enantiomer of 9 (24.9 min) for an 83% ee in the product 9.

Employing the procedures substantially as described in the above Example, but with various solvents and solvent mixtures, and chiral modifiers the results shown in the following Table were realized:

TABLE

Asymmetric alkyne addition summary

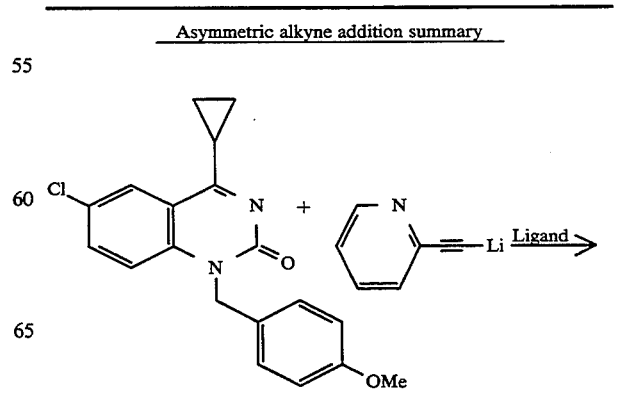

TABLE-continued

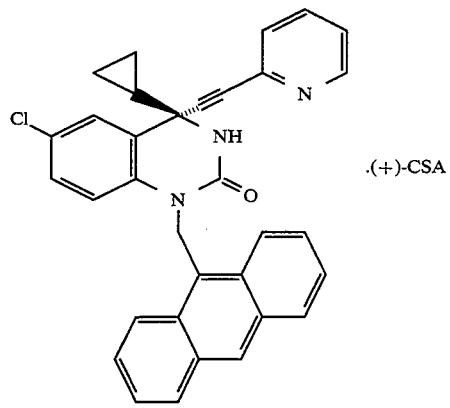

| Entry | Ligand[1] | equiv. | solvent[2] | temp (°C.)[3] | ee (%) |
|---|---|---|---|---|---|
| 1 | Quinine | 1 | THF | −20 | 48 |
| 2 | Hydroquinine | 1 | THF | −20 | 64 |
| 3 | Quinidine | 1 | THF | −20 | −55 |
| 4 | Hydroquinidine | 1 | THF | −15 | −39 |
| 5 | Cinchonidine | 1 | THF | −30 to −10 | 26 |
| 6 | Quinine | 0.25 | THF | −20 | 17 |
| 7 | Quinine | 1.5 | THF | −20 | 41 |
| 8 | Quinine | 1 | Et₂O | 20 | 36 |
| 9 | Quinine | 1 | Toluene | 20 | 28 |
| 10 | Hydroquinine | 1 | THF/Tol (1:1)[4] | −15 | 75 |
| 11 | Hydroquinine | 1 | Tol/THF (5:1) | −15 | 66 |
| 12 | Hydroquinine | 1 | THF/Hex (6:4) | −15 | 83 |
| 13 | Quinine (Mg) | 1 | THF | 50 | −12 |
| 14 | Quinine (Na) | 1 | THF/Hex (1:1)[5] | −20 | −9 |
| 15 | Ephedrine | 1 | THF | −25 | 6 |
| 16 | N-Methyl-prolinol | 1 | THF | −20 | 0 |
| 17 | Hydroquinine 4-methyl-2-quinolyl ether | 1 | THF | −20 | 0 |
| 18 | Sparteine | 1 | THF | −15 | 0 |

[1]Enough n-BuLi (EtMgBr entry 13, NaN(TMS)₂ entry 14) was added to deprotonate alkyne and any ligand group.
[2]Reactions were run at 75 mM in alkyne unless otherwise noted.
[3]Deprotonation and imine addition were carried out at −75 to −45° C., then mixture was warmed to noted temperature.
[4]Same ee at 75 mM and 38 mM.
[5]Lower yielding reaction.

EXAMPLE 2

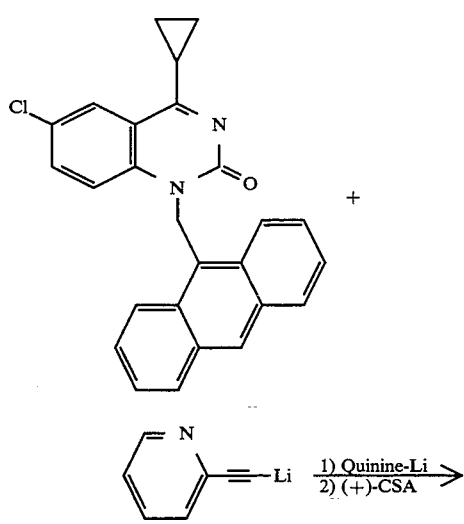

50 L cylindrical vessel equipped with a cooling bath, nitrogen sparge line, and an addition funnel was rinsed with dry THF and charged with dry THF (21.0 L). The solvent was dried to 23 μg H₂O/mL by pumping through a 1 L column of 4A molecular sieves while nitrogen was bubbled into the vessel. Quinine (1278 g) and 2-ethynylpyridine (sieve dried, 372 mL) were added and the solution was further sparged with nitrogen. The addition funnel was charged with n-BuLi (4.55 L of 1.72 M in hexanes) and the stirred solution was cooled to −52° C. Addition of n-BuLi was carried out over 60 minutes, with the temperature rising as high as −38° C. The solution was then warmed to −25° C. over 60 minutes. The solid quinazolinone (1080 g) was added in one portion, and the resulting suspension was stirred at −25° C. After 14 hours the suspension was warmed to −20° C. 2 M H₂SO₄ (10 L) was slowly added via the addition funnel, causing warming to 5° C. The mixture was diluted with 10 L saturated aq. NaCl and transferred to a 100 L cylindrical vessel, rinsing with 6.6 L THF. Saturated. aq. NaCl (10 L) was added and the mixture was agitated, then allowed to settle and the layers were separated. The organic layer contained 1146 g, 86.5 % at 94 area % purity (220 nm) and >97 % ee. The organic layer was dried over MgSO₄, then filtered. The volume was reduced to 15 L by vacuum distillation. The stirred solution was treated with (+)-camphorsulfonic acid (611 g), giving first a clear solution, then crystallization after 10 minutes. After 14 hours, the product salt was collected by filtration, washed with a small volume of THF and dried at 37° C. under vacuum with nitrogen sweep. Yield of the THF solvate was 1823 g of 88.6 weight % salt, 83.8% yield. Purity was 99 area %; ee was >98%.

REMOVAL OF PROTECTING GROUP

Preparation of 10 (R=p-methoxybenzyl)

A quantity of 70 mg (0.16 mole) of 9 was treated with a solution of 3.2 ml of trifluoroacetic acid in 4.5 ml of methylene chloride for 96 hours under argon. The solvents were evaporated and the residue was partitioned between CHCl₃ and 10% w/v aqueous Na₂CO₃. The organic layer was dried over Na₂SO₄, filtered and evaporated to 38 mg of an amorphous solid (73%).

NMR (CDCl₃): δ 0.58–0.72 (m, 1H), 0.73–0.90 (m, 2H), 0.91–1.04 (m, 1H), 1.47–1.60 (m, 1H), 5.85 (s, 1H), 6.78 (d, J=8 Hz, 1H), 7.15 (dd, J=8, 2Hz, 1H), 7.20–7.28 (m, 1H), 7.39 (d, J=8 Hz, 1H), 7.52 (d,

J=2Hz, 1H), 7.63 (td, J=8, 2Hz, 1H), 8.58 (d, J=4Hz, 1H), 9.13 (s, 1H).

Preparation of 10 (R=9-anthrylmethyl)

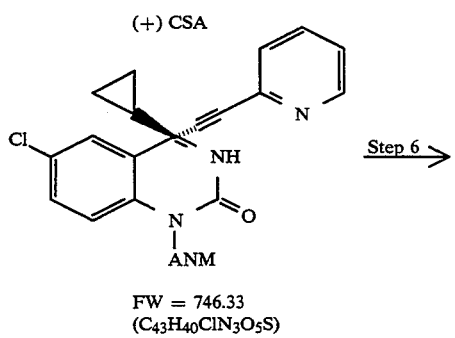

FW = 746.33
(C43H40ClN3O5S)

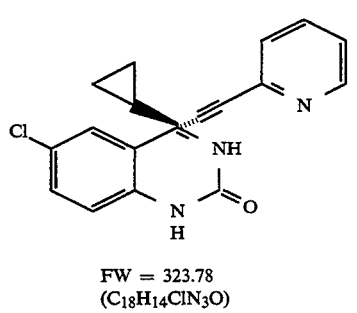

FW = 323.78
(C18H14ClN3O)

Preparation of 10 (R=9-anthrylmethyl)

To a 12 L three necked round bottom flask equipped with a nitrogen inlet, a thermocouple probe, an overhead stirrer, was added anisole (1.8 L) and trifluoroacetic acid (2 L). The mixture was cooled down to 12°-13° C. To this solution was added the (+)-camphorsulfonic acid salt (1.7 kg), keeping the batch temperature below 25° C. and rinsing with trifluoroacetic acid (0.55 L). The mixture became homogeneous. The solution was stirred at room temperature for 23 hours. The starting material should be below 1A% by HPLC after 23 hours. The mixture was concentrated below 50° C. in vacuo. The residue was dissolved in ethyl acetate (8.5 L). The solution was treated with saturated aqueous sodium chloride solution (6.2 L) then cooled to 13° C. To the mixture was added 10 wt % sodium hydroxide (ca. 6 L), keeping temperature below 30° C. The pH of the aqueous layer was 8.5. The organic layer was separated and washed with saturated aqueous sodium chloride solution (3 L). The extract (12 L) was concentrated in vacuo and the residue was dissolved in methanol (6.8 L). Water (140 mL) was added and the mixture was stirred at room temperature overnight. The precipitates were filtered off and washed with 98% methanol (3.4 L). The flitrate and wash were combined and subjected to the resin chromatography [SP 206; 17 L of resin; eluted with 2 v/v % water in methanol]. The fractions containing 10 were combined, concentrated in vacuo, and dissolved in ethyl acetate (6.8 L). The solution was stirred at room temperature overnight. The resultant crystals were filtered off and washed successively with ethyl acetate (1 L) and 1:1 mixture of ethyl acetate and hexanes (3 L). The crystals were dried at 40° C. in the oven to give 545 g of 10 as an ethyl acetate solvate. The crystals (540 g) were suspended in water (12 L) and heated up to 100° C. to remove ca. 4 L of water by distillation. The mixture was cooled to room temperature. The crystals were filtered off and washed with water (2 L) and dried under a nitrogen stream to give 532 g of 10 (R=9-anthrylmethyl) monohydrate (78% yield).

What is claimed is:

1. A process for the preparation of a compound of structural formula:

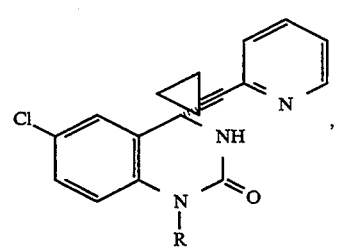

wherein R is —CH2—A, and A is
  i) phenyl unsubstituted or substituted one or more times with B, wherein B is C1-4 alkyl, C1-4 alkoxy, or halo;
  ii) naphthyl unsubstituted or substituted one or more times with B; or
  iii) anthryl unsubstituted or substituted one or more times with B;

said process comprising the steps of:
  (a) mixing one equivalent of 2-ethynylpyridine with about one equivalent of a chiral modifier selected from quinine or dihydroquinine, in a solvent comprising an ethereal solvent selected from THF, diethyl ether, 1,2-dimethoxyethane or dioxane, said ethereal solvent optionally combined with toluene, hexanes, or other less polar solvents;
  (b) mixing thereto, at between about −70° to about −20° C., two or more equivalents of either n-butyl lithium or lithium hexamethyldisilazane;
  (c) mixing thereto, between about 0.5 and 1.0 equivalents of a compound of structural formula

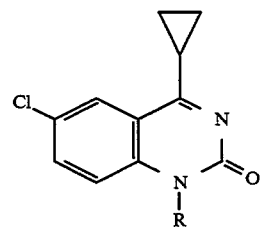

at about −50° to 0° C.;
  (c) maintaining the resulting mixture at about −40° C. to about 0° C. for 2–24 hours;
  (d) to give a compound of Formula I.

2. The process of claim 1 wherein the ethereal solvent is THF or diethyl ether.

3. The process of claim 2, wherein the chiral modifier is dihydroquinine.

4. The process of claim 3 wherein the solvent is a mixture of THF and hexanes or a mixture of THF and toluene.

5. The process of claim 4 wherein the solvent is THF and hexanes (6:4 v/v).

6. The process of claim 1 wherein R is p-methoxybenzyl or 9-anthrylmethyl.

7. The process of claim 2 wherein R is p-methoxybenzyl or 9-anthrylmethyl.

8. The process of claim 3 wherein R is p-methoxybenzyl or 9-anthrylmethyl.

9. The process of claim 4 wherein R is p-methoxybenzyl or 9-anthrylmethyl.

10. The process of claim 5 wherein R is p-methoxybenzyl or 9-anthrylmethyl.

11. A compound of structural formula:

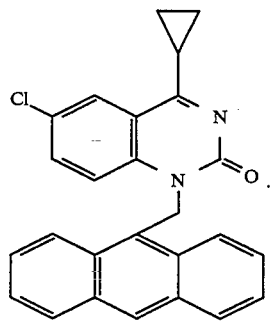

12. The process, according to claim 1, for the preparation of a compound of structural formula:

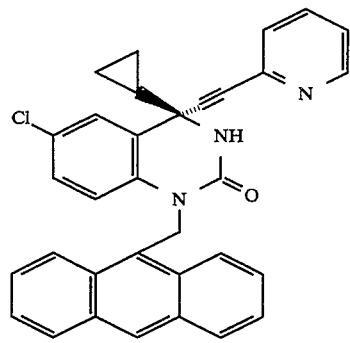

said process comprising the steps of:
  (a) mixing, in a solvent comprising THF, about one equivalent of 2-ethynylpyridine with about one equivalent of the chiral modifier quinine;
  (b) cooling the mixture to between about −40° C. and about −60° C.;
  (c) adding thereto about 2.0 equivalents of n-butyllithium;
  (d) warming the reaction mixture to about −25° C.;
  (e) adding between about 0.5 to 1.0 equivalents of the quinnazolinone

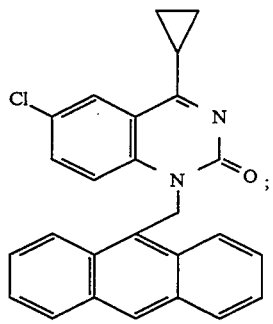

(f) stirring the resulting mixture at about −25° C. for about 16 hours to give the compound of formula II.

* * * * *